United States Patent
Bækgaard

[11] Patent Number: 6,134,331
[45] Date of Patent: Oct. 17, 2000

[54] ELECTRONIC STETHOSCOPE

[75] Inventor: Knud Erik Bækgaard, Holstebro, Denmark

[73] Assignee: Bang & Olufsen Technology A/S, Struer, Denmark

[21] Appl. No.: 08/793,622

[22] PCT Filed: Aug. 30, 1995

[86] PCT No.: PCT/DK95/00349

§ 371 Date: Feb. 28, 1997

§ 102(e) Date: Feb. 28, 1997

[87] PCT Pub. No.: WO96/06562

PCT Pub. Date: Mar. 7, 1996

[30] Foreign Application Priority Data

Aug. 30, 1994 [DK] Denmark ................................ 1005/94

[51] Int. Cl.[7] .................................................. A61B 7/04
[52] U.S. Cl. ........................................................ 381/67
[58] Field of Search ................................................ 381/67

[56] References Cited

U.S. PATENT DOCUMENTS

| | | | |
|---|---|---|---|
| 4,425,481 | 1/1984 | Mansgold et al. | 381/317 |
| 4,598,417 | 7/1986 | Deno | 381/67 |
| 5,481,615 | 1/1996 | Eatwell et al. | 381/71.11 |
| 5,539,831 | 7/1996 | Harley | 381/67 |
| 5,602,924 | 2/1997 | Durand et al. | 381/67 |

*Primary Examiner*—Ping Lee
*Attorney, Agent, or Firm*—Sixbey, Friedman, Leedom & Ferguson; David S. Safran

[57] ABSTRACT

An electronic stethoscope consisting of a transducer, an amplifier and a headphone will be better adapted to the habits of use of doctors when it is supplied with filters which mimic the transfer function of acoustic stethoscopes. Thus, the signals heard will correspond to those learnt, and thereby the advantages of greater amplification and elimination of noise sources may be fully utilized. Hence there is a possibility for extended digital signal processing which may furthermore compensate for the hearing loss of each individual doctor.

15 Claims, 2 Drawing Sheets

ELECTRONIC STETHOSCOPE

The invention relates to an electronic stethoscope of the type comprising a vibration transducer, an amplifier, and a headphone arrangement.

Stethoscopes are used by physicians to listen to sounds from the organism, in particular heart and lungs. The phenomena listened for emit sounds with frequencies from below 16 Hz to about 8 kHz, but a serious low pass filtering occurs during the passage of tissue and skin. The skin acts like a transmitter of those signals which are subsequently accessible. The construction of the stethoscope ascertains that only a small area of the skin is listened to at a time, and that sounds in the room outside are dampened, and thus the signal-to-noise ratio is somewhat improved. Physicians train actively in the use of stethoscopes, and thereby their ability to distinguish signals in the surrounding noise may rise by about 15 dB. This occurs the world over, and one might say that a stethoscope is a universal tool. However, its value and/or performance to the users have fallen, due to the technical development of society. The increased machine noise, in particular in hospitals, in practice causes the signals to lie below or at the most at the lower limit of human hearing. To this may be added that more and more young persons suffer from hearing loss at the time they may embark on a medical education, and hence the acoustic stethoscope has in practice reached its limit of performance.

It has long been realized that a traditional acoustic stethoscope introduces many linear distortions in its signal transmission, in particular because of the possibility for standing waves in the long tubes. This may be expressed differently by stating that the bad impulse response causes a strong distortion of the temporal reproduction of the signals. Traditionally, there are various constructions of stethoscopes, and they each have their individual characteristic transfer function, and one may to a certain degree, by changing acoustical stethocscope, obtain a more distinct representation of a given acoustic phenomenon. However, the physician's reliability in using stethoscopes is generally so large, in particular when using the stethoscope they have become used to, that the impulse response problem has not been regarded as a bar to the use of acoustic stethoscopes.

For this reason it has not been attractive to use an electronic stthoscope, even though it gives the possibility of active amplification to any desired degree. Even though there are furthermore very improved possibilities for adapting the sensitivity of a vibration transducer to the body being measured upon, and even though headphones with a high damping may act as better insulators against surrounding noise than ordinary earpieces of a traditional stethoscope, an electronic stethoscope still meets resistance, in particular because it does not "sound like they used to", due to the wider frequency band and the consequent larger content of noise. The ability to distinguish phenomena which has laboriously been learnt by the physician does not help any longer.

It has been recognized that there is a need for amplifying certain frequency areas relative to those which are effectively reproduced by an acoustic stethoscope. A known construction of an electronic stethoscope is described in U.S. Pat. No. 5,003,605 which electronically performs a lifting of these wider frequency areas and performs a frequency conversion for very low frequency areas. In this way certain phenomena are given an improved clarity. Furthermore the stethoscope is connected to electrodes and electrocardiographic circuits for the recognition of the QRS complex in order that signals representing the electrical activity of the heart may be brought to the ear simultaneously with the heart sounds so that the temporal relationship of the sounds in relation to the heart cycle may be evaluated.

It has been recognized in the invention that it will be possible to obtain a considerably improved stethoscope which has both the advantage of a larger amplification and of knowledgeable analysis by a physician, who will not be confused by a changed sound characteristic, provided that there is in the signal path of an otherwise linear electronic stethoscope connected a filter with an impulse transfer function which corresponds to at least one known acoustic stethoscope. This means that temporal relationships are now reproduced as if they were transmitted through the said acoustic stethoscope. Thus there is in a very advantageous manner obtained an interaction between man and auxiliary equipment. By an A/B comparison between the linear sound and the simulated stethoscope sound certain phenomena may be recognized which were not as clear in traditional stethoscopy. Furthermore there is a possibility to permit physicians to discuss the same phenomenon during simultaneous ausculation, as several headphones may well be connected to one and the same amplifier with filter.

With the access to modern technology it is obvious that digital filtering will be used, because it permits reprogramming without lengthy calibration. This also opens possibilities for letting the electronic stethoscope store filter transfer functions which correspond to the known main types of stethoscopes (small and large cup, with or without membrane) in order that the physician using it has only to select the filter function which corresponds best to the type of stethoscope that this particular physician has the best training in—or which according to traditional teaching is found as best suited to the task. In this respect it will also be feasible to let digital signal processing adapt the filter to the signal whereby a real improvement in the signal-to-noise ratio is obtained.

While using digital signal processing the stethoscope according to an embodiment of the invention contains pattern recognition means for the acoustic signal for adaptive reduction of noise from the surroundings as well as suppression of repetitive signals in the ausculated signal. Hereby e.g. the sound of heartbeats may be reduced when ausculating lungs, or the heart sound of the mother may be reduced while performing fetal ausculation.

Similarly a further embodiment establishes a reference to the heart sound, in that the pattern recognition means are used for eliminating, respective enhancing parts of repetitive signals in the signal listened to. Thus it becomes possible to diagnose sounds due to disease in the heart and surrounding arteries, and a "windowing function" is enabled where only part of a heart cycle is listened to, e.g. the systole. Correspondingly one may synchronize to the respiration when performing examination of the respiratory passages/lungs.

In that it has been realized in the invention that it is possible and extremely advantageous to perform signal processing in the passage from transducer to ear, there is similarly enabled the possibility that further signal processing may improve analyses made by stethoscope. As an example may be mentioned that the electronic stethoscope can be adapted to the individual hearing loss of the physician, e.g. by having this measured objectively and converted to a transfer function which is stored in the electronic stethoscope according to the invention. In this connection there may well be included dynamic limitations so that a certain sound pressure is not exceeded, possibly only in certain frequency bands. It is furthermore advantageous that the sound is brought to the ear as close to the ear canal as possible, in that there is thereby no further influence on the signal which has been corrected in earlier stages. In the case of A/B comparisons between compensated and non-compensated sound such a dynamic limitation will be similarly important.

With a view to prevent disturbing noises during the movement of the measuring transducer of the stethoscope from one place to another, possibly during rubbing on the skin, the stethoscope according to the invention is provided with an automatic amplification control so that the sensitivity of the ear is preserved, because it is not subjected to sudden strong sounds.

As the construction of digital filters is so flexible it becomes simple and economically justifiable to perform an individual adjustment for each of the ears of a physician, in such a way that there are two channels or one multiplexed channel with filters. Apart from this it will only require two transducers and two preamplifiers to obtain a stereophonic electronic stethoscope, as the transducers may be placed such on a body to be examined that the sound production appears spatial through the headphones.

A further improvement of the functionality of the electronic stethoscope if it can be made hands-free. This is obtained in an advantageous manner in that there is established a wireless (high frequency, low frequency, or optical) link between the transducer part and the head phone part. In this manner listening-in is also enabled, as another listener need only bring his own headphone with receiver for the wireless link. Dependent on the degree of personal signal processing to be performed in the electronic stethoscope, vide supra, the interface between that which is to be inside the central transmitter part and that which is to be inside the headphone is selected at the planning of the system. In order for a system to be complete it will also be relevant to introduce a speech channel, i.e. a microphone with amplifier and transmitter into which the surroundings and the physicians themselves fitted with headphones speak, so that the speech is coupled to the headphones in a wireless fashion, whereby it becomes possible to communicate with the physicians or at least to place emergency calls, even though they are isoleted completely from the outside world by the headphones.

Complete hands-free operation will only be possible if the transducer part can remain by itself on the skin of the patient. From in particular neo-natal departments it is known to use straps, but this only creates a proximity, not necessarily a secure and uniform contact to the skin. In connection with the invention it has been found advantageous to adhere the transducer part by means of suction from a small vacuum pump whereby there is also obtained a calibrated distention of the skin, so that a more reproducible contact is obtained. Alternatively it may be a particular advantage in connection with an acceleration transducer to use a double-faced adhesive strip. Correspondingly, a separate transducer part may be devised in such a way that it may be held under a blood pressure measuring cuff.

Such an improvement in the reproducibility is a prerequisite for obtaining a meaningful result when storing a sound which has been determined during an examination, in order to compare it to a corresponding sound determined later. This sound may be repeated cyclically according to requirements so that weakly represented characteristics may be more easily identified. A series of such sounds may be stored electronically with a view to A/B comparisons. It is quite feasible to store a patient's individual, established sound on a medium which is attached to the file and which may be replayed at a later examination in order that a concrete comparison may be performed and hence a much more precise evaluation of a development, even though several independent physicians might perform the examinations. This sound may equally be stored in the stethoscope itself and may be recalled by entering a code. It would be most relevant to store the unfiltered sound which during comparison is subjected to the same filtering as the direct sound in the stethoscope according to the basic principle of the invention. Correspondingly, it may be expedient to let the stethoscope contain a store for a number of standard sounds which may be recalled for the identification and/or characterization of a new sound.

In case it is desirable to make the transition from a particular stethoscope to the electronic stethoscope particularly unproblematic for the individual physician, his or her private stethoscope may be measured in order to obtain its transfer function, whereupon a filter function closely corresponding to it is established and stored in the electronic stethoscope. A gradual "un-learning" of the set habits may be obtained by also storing a series of corresponding filter functions with gradually less pronounced resonances and antiresonances, all seen as a gradual transfer to the linear amplification. By performing a training programme it will be possible to obtain a complete adjustment to only using linear amplification.

The invention will be described in greater detail with reference to the drawing, in which FIG. 1 shows a typical transfer function of a traditional stethoscope, FIG. 2 shows a block diagram of the basic principle of a stethoscope according to the invention.

Figure 1:
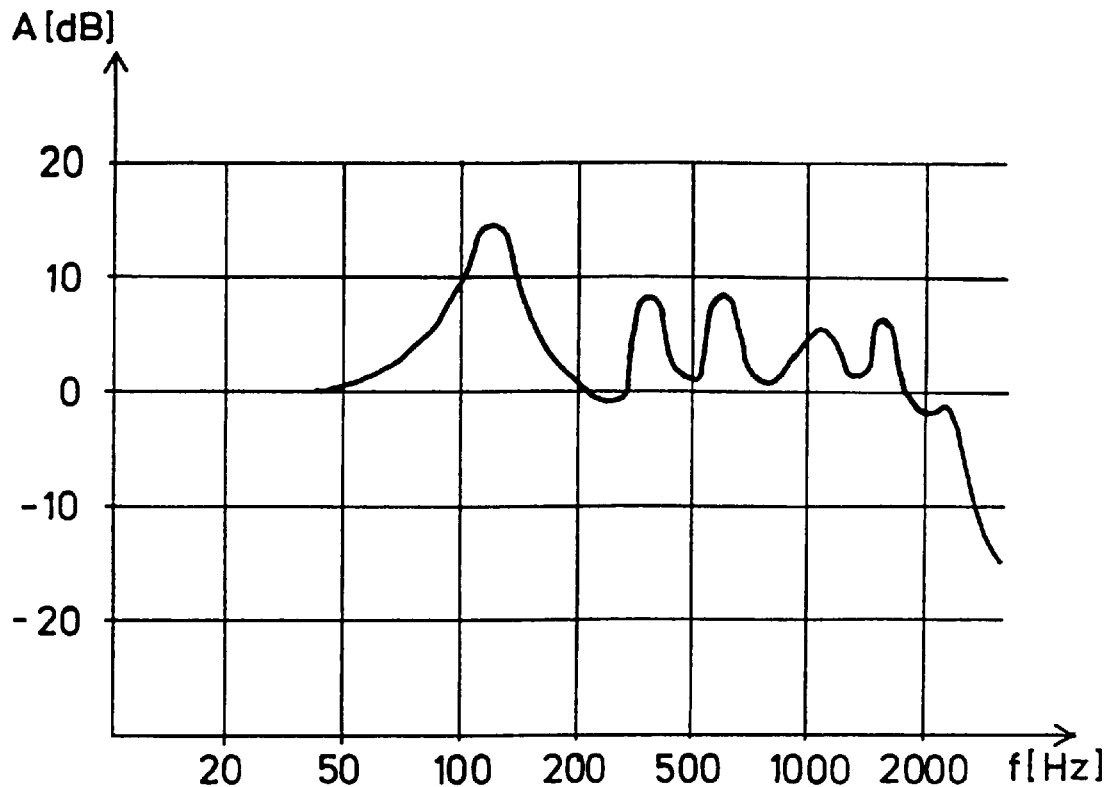

In FIG. 1 is shown a generalised transfer function for a type of stethoscope which is widely used, i.e. a funnel with two outlets and individual tubes to each ear. It will be seen that there are pronounced resonances and antiresonances which apart from an amplitude distortion also will give rise to a delay distortion which will make the determination of transients difficult.

Figure 2:
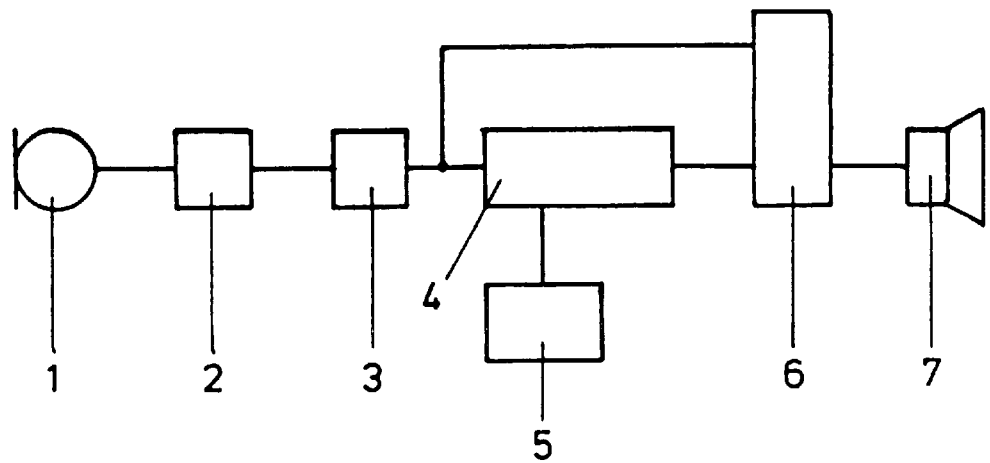

In FIG. 2 is seen a block diagram for an electronic stethoscope according to the invention. A vibration transducer 1 is sued for transferring the signal from the surface of the skin to the apparatus. It may be any kind of transducer, such as a microphone or an accelerometer, i.e. sensitivity towards position, velocity or acceleration. A preamplifier 2 performs impedance conversion and pre-emphasis (integration in the case of an accelerometer) takes place in the amplifier 3. There may also be performed a pre-emphasis in dependence of the thickness of fatty and other tissue which is placed between the sound source (e.g. the heart) and the transducer. The choice of transducer is made on the basis of considerations as to signal-to-noise ratio and the pre-emphasis desired. The unit 4 contains an analog-to-digital converter (A/D converter), a digital filter, and a digital-to-analog converter (D/A converter), in order that a filtered signal may be brought to the output amplifier 6. As shown there is furthermore brought a direct signal from the preamplifier 3, in order that an A/B comparison may be made between the signal filtered in 4 and the unfiltered signal. Before such a comparison is performed, there may be a loudness equalization between the two channels so that the ear will not have too great adjustment problems by the comparison. From the output amplifier the amplified signal is brought to one or several headphones which are only shown as a loudspeaker 7.

In order to be able to switch between several transfer functions for the filter, either different in appearence or in principle of the same kind but less pronounced, in store 5 there is stored tables of the filter coefficients needed in order to obtain the desired transfer function for the digital filter. Such a selection of coefficients falls within the general knowledge of the skilled person. It is obvious that other types of digital filter may be selected where the determining parameters are stored in another way than by storing coefficients. One of the transfer functions mentioned may be obtained, not as a representative transfer function of a type of stethoscope but as the result of a concrete measurement on an individually selected stethoscope.

EXAMPLE

Figure 3:
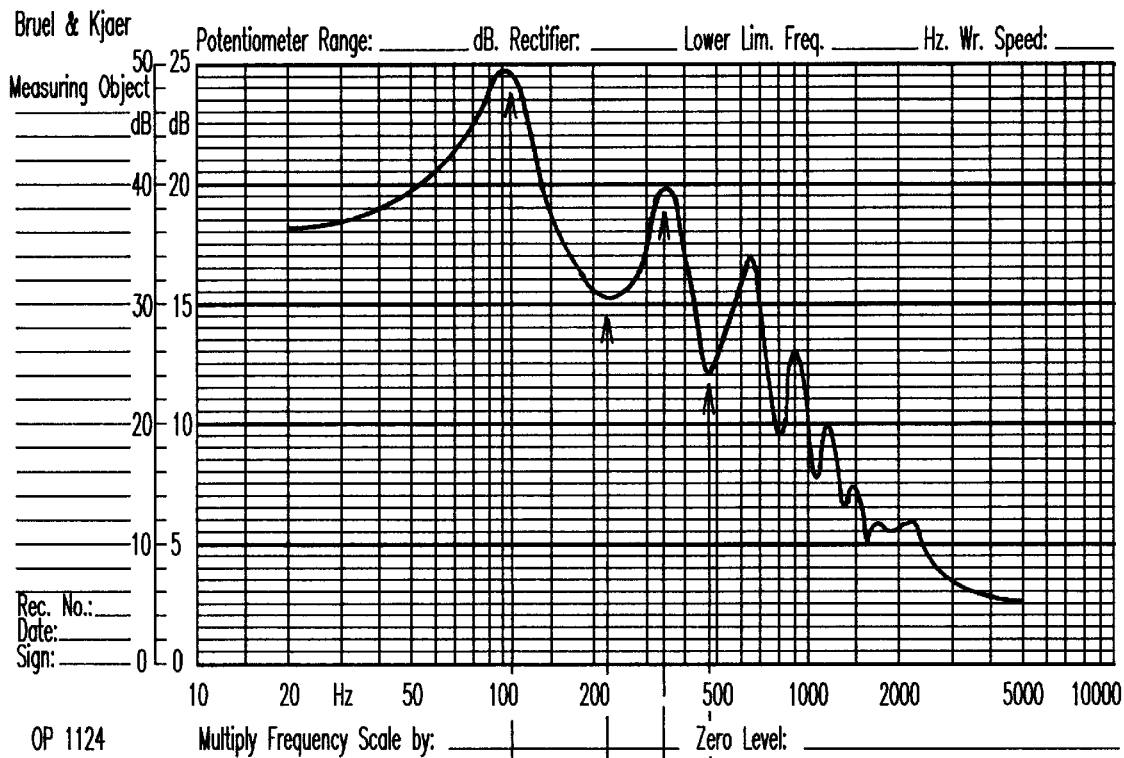
FIG. 3 is graph representing a transfer function measured from Littman Classic II stethoscope.
Figure 4:
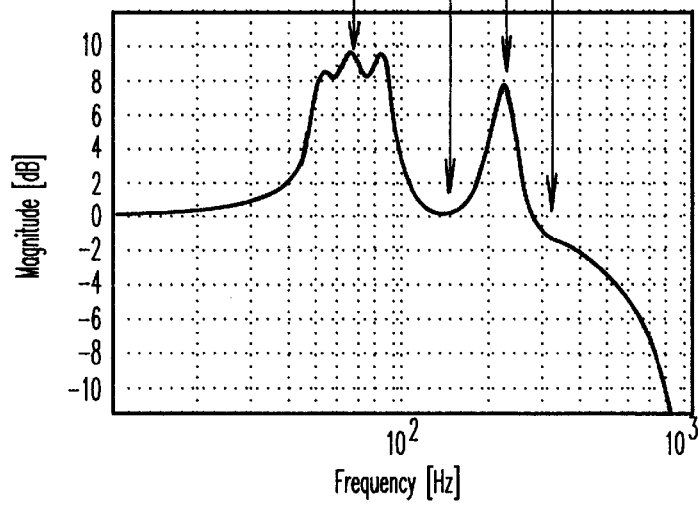
FIG. 4 is a transfer function produced in accordance with the present invention which is equivalent to the measured transfer function of FIG. 3.

A Littman Classic II stethoscope was measured by two methods. On the one hand the mechanical dimensions were measured, and the electroacoustic equivalent circuit was developed in the situation where the stethoscope was in contact with the skin as the transmitter and the ear pieces inserted in the ear canal. On the other hand one unit was measured in a standard Brüel & Kjær acoustic measuring setup with a sweep oscillator and filter and a plotter. In FIG. 3 is seen the measured transfer function. On the basis of a calculation of the transfer function by means of the electroacoustic equivalent the filter coefficients for a digital filter were calculated according to standard practice for the first resonance peaks in the transfer function. These coefficients are reproduced in Table 1. The coefficients are stored in a programmable memory device type 27C512 (pos. 5 in FIG. 2), and are used in a digital signal processing device type ADSP2101 (pos. 4 in FIG. 2). The detailed signal connections between the devices are assumed known to the skilled person. Hereby the transfer function reproduced in FIG. 4 is obtained. Different units are used on the frequency axes, because the digital signal processing was performed at a clock frequency which deviated from that which would cause the two transfer functions discussed to relate to identical frequency ranges. In the figures, this constant factor has been taken account of, and arrows show the correspondance between resonances and antiresonances in the measured transfer function and that obtained by digital signal processing.

In a completely analogous manner, the digital filter may be expanded to comprise the resonances and antiresonances having a smaller amplitude, the filter order being higher. Use of the electroacoustic equivalent circuit as the basis immediately gives the possibility of obtaining a correct impulse response, and an acoustic measurement which also comprises the phase function may be used in a corresponding manner.

TABLE 1

Filter coefficients for electronic stethoscope (digital filter)

First resonator (2nd order IIR filter)

A0 = 0.167283222079277039
A1 = −0.331625401973724365
A2 = 0.164647430181503296
B0 = 1.000000000000000000
B1 = −1.989778280258178710
B2 = 0.991558074951171875

TABLE 1-continued

Filter coefficients for electronic stethoscope (digital filter)

Second resonator

A0 = 0.168205320835113525
A1 = −0.330643445253372192
A2 = 0.163203150033950806
B0 = 1.000000000000000000
B1 = −1.983934164047241210
B2 = 0.988377273082733154

Third resonator

A0 = 0.167822774839401245
A1 = −0.331159085035324097
A2 = 0.164011687040328980
B0 = 1.000000000000000000
B1 = −1.987000107765197750
B2 = 0.989760994911193848

Fourth resonator

A0 = 0.247263073921203613
A1 = −0.472294241189956665
A2 = 0.232113614678382874
B0 = 1.000000000000000000
B1 = −1.948417305946350100
B2 = 0.977224946022033691

FIR filter (7th order). All coefficients are multiplied by 4!

h(1) = 0.304660081863403320
h(2) = 0.512181341648101807
h(3) = 0.68066960573#964111
h(4) = 0.745538234710693359
h(5) = 0.680669605731964111
h(6) = 0.512181341648101807
h(7) = 0.304660081863403320

What is claimed is:

1. An electronic digital stethoscope comprising a vibration transducer, an amplifier, a headphone arrangement, and a digital filter means which establishes at least one impulse transfer function corresponding to at least one acoustic stethoscope type; and wherein in the signal path before the filtering, there is performed a pre-emphasis of the high frequencies in dependence of the thickness of tissue which is present between an actual sound source and the transducer.

2. A stethoscope according to claim 1, further comprising digital filter means providing pre-emphasis.

3. A stethoscope according to claim 2, wherein multiple impulse transfer functions corresponding to multiple stethoscope types are stored in conjunction with the digital filter.

4. A stethoscope according to claim 1, further comprising means for an A/B comparison between the linear sound before filtering and the sound after digital filtering.

5. A stethoscope according to claim 4, wherein the sound after digital filtering is monitored prior to being routed to the head phone arrangement.

6. A stethoscope according to claim 1, wherein multiple headphones are coupled to one and the same amplifier.

7. A stethoscope according to claim 1, wherein the impulse transfer function of the digital filter means is obtained by measurement on a concrete stethoscope.

8. A stethoscope according to claim 1, further comprising digital pattern recognition means for windowing the acoustic signal to adaptively remove noise from the surroundings and suppress repetitive signals in the observed signal.

9. A stethoscope according to claim 8, wherein the digital pattern recognition means removes repetitive signals from the observed signal.

10. A stethoscope according to claim 8, further comprising means for an A/B comparison between the linear sound before filtering and after filtering.

11. A stethoscope according to claim 10, wherein the sound after digital filtering is monitored prior to being routed to the head phone arrangement.

12. A stethoscope according to claim 1, further comprising means for automatic control of amplification.

13. A stethoscope according to claim 1, wherein the headphone arrangement consists of transducers which are fitted in immediate proximity to the ear canal in each ear.

14. A stethoscope according to claim 13, wherein the signal to each ear is compensated with respect to the sensitivity of the particular ear.

15. A stethoscope according to claim 1, wherein the digital filter means stores multiple impulse transfer functions, each corresponding to a different acoustic stethoscope type, and wherein a user can select a desired one of the impulse transfer functions.

* * * * *